US00PP32590P3

(12) United States Plant Patent
Biancheri

(10) Patent No.: US PP32,590 P3
(45) Date of Patent: Dec. 8, 2020

(54) ***RANUNCULUS* PLANT NAMED 'ABORIONE'**

(50) Latin Name: *Ranunculus asiaticus*
Varietal Denomination: ABORIONE

(71) Applicant: Impresa Individuale Biancheri Alberto, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 16/873,431

(22) Filed: Apr. 10, 2020

(65) Prior Publication Data

US 2020/0352072 P1 Nov. 5, 2020

(30) Foreign Application Priority Data

May 2, 2019 (QZ) ..... PBR 2019/1128

(51) Int. Cl.
*A01H 5/02* (2018.01)
*A01H 6/00* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A new and distinct cultivar of *Ranunculus* plant named 'ABORIONE' is disclosed, characterized by uniquely colored flowers having purple and white striated petals with long pedicels and a typical vase life of 20 to 25 days. Plants have a unique foliage carriage, with foliage occurring densely at the base of the plant. The new variety is a *Ranunculus*, normally produced as a cut flower and potentially useful as an ornamental plant.

1 Drawing Sheet

Latin name of the genus and species: *Ranunculus asiaticus*.

Variety denomination: 'ABORIONE'.

BACKGROUND OF THE INVENTION

The new *Ranunculus* cultivar is a product of a planned breeding program conducted by the inventor, Alberto Biancheri at a research nursery in Camporosso Mare, Italy. The cross resulting in this new variety was made during 2013.

The seed parent is the, unpatented, proprietary variety referred to as *Ranunculus* '220-07/1'. The pollen parent is the unpatented, proprietary variety referred to as *Ranunculus* '146-10.6'. The new variety was discovered in 2015 by the inventor in a group of seedlings resulting from the 2013 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2015 and has shown that the unique features of this cultivar are stable and reproduced true to type in multiple successive generations.

SUMMARY OF THE INVENTION

The cultivar 'ABORIONE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABORIONE' These characteristics in combination distinguish 'ABORIONE' as a new and distinct *Ranunculus* cultivar:

1. Unique purple and white striated petals.
2. Long pedicels.
3. Low foliage carriage, flowers occurring high above a low growing plant.
4. Long vase life.
5. Flower diameter of 6 to 8 cm.

PARENT COMPARISON

Plants of the new cultivar 'ABORIONE' are similar to plants of the seed parent, in most horticultural characteristics, however, plants of the new cultivar 'ABORIONE' differ in the following;

1. Flowers of the new variety are a different color than those of the seed parent.
2. Flowers of the new variety are larger than flowers of the seed parent.

Plants of the new cultivar 'ABORIONE' are similar to plants of the pollen parent, in most horticultural characteristics, however, plants of the new cultivar 'ABORIONE' differ in the following;

1. Flowers of the new variety are a different color than those of the pollen parent.
2. Vegetative carriage of the new variety is lower than that of the pollen parent.

COMMERCIAL COMPARISON

Plants of the new cultivar 'ABORIONE' are comparable to the commercial variety *Ranunculus* 'ABLEIGONG', U.S.

Plant Pat. No. 30,023. The two *Ranunculus* varieties are similar in most horticultural characteristics; however, the new variety 'ABORIONE' differs in the following:

1. Foliage of this comparator is denser and wider.
2. Petals of the new variety has striations, whereas petals of 'ABLEIGONG' are solid and less lavender shaded.

BRIEF DESCRIPTION OF THE PHOTOGRAPH

The accompanying photograph illustrates a close-up view of individual flowers on flowering plants of the new variety at approximately six months old, grown in a greenhouse during April in Camporosso, Italy. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 5-month-old 'ABORIONE' plants grown in a greenhouse in Camporosso Mare, Italy. The plant has been described in the month of February. In order to protect the crop against pests, some chemical treatments are performed. Treatments with growth regulators can be performed to limit the plant sizes. In particular, no growth regulators have been applied on the plant described. The rhizome has been planted on raised benches in a peat and pumice substrate mixture. The growing temperature ranged from 12° C. to 26° C. during the day and from 0° C. to 6° C. during the night. General light conditions are bright, normal sunlight. Measurements and numerical values represent averages of typical plant types.

Botanical classification: *Ranunculus asiaticus* 'ABORIONE'.

PROPAGATION

Time to rooting: 15 days at approximately 10-12° C.
Time to produce a rooted plantlet: 20 days.
Root description: Tuberous root.

PLANT

Growth habit: Herbaceous perennial, semi-prostrate vegetation.
Height to top flower: 40 to 50 cm.
Leaf height: 30 to 40 cm.
Plant spread: 40 to 45 cm.
Growth rate: Medium.
Branching characteristics: Main floral stems grow from a basal rosette with 1 or 2 lateral branches, each one of which has one or more flowers.
Length of lateral branches: 35 to 45 cm.
Diameter of lateral branches: 6 to 8 mm.
Texture of lateral branches: Slightly tomentose.
Internode length: Internodes are extremely close together, forming a basal rosette.
Strength of lateral branches: Strong.
Color of lateral branches: Near RHS Yellow-Green 144A.
Aspect/angle of branches: 10° to 15°.
Number of leaves per lateral branch: Usually 2 or 4.

FOLIAGE

The plant has a marked heterophylly that means that in the same plant the leaves may have different size and arrangement (simple, ternate and bitemate), in relation to the degree of development (young leaf and mature leaf) and their position on the plant (basal leaf—leaf at the base of the plant—and cauline leaf—leaf inserted at the nodes of the floral stems). In other words, there are significant variation in leaf shape on a same plant.

Leaf at the base of the plant:

*Arrangement*.—Simple (young leaf); Ternate (mature leaf).
*Average length*.—25 to 30 cm.
*Average width*.—10 to 15 cm.
*Overall shape of blade*.—Obovate (young leaf); Palmatipartite (mature leaf).
*Dissected leaves, describe lobes, quantity of dissection*.—Young leaves are generally not lobed or a little lobed; mature leaves are generally divided in 3 parts, each one of which is further divided in 3 or more lobes.
*Apex*.—Rounded.
*Base*.—Acute.
*Attachment*.—Petiolate.
*Margin*.—Dentate.
*Texture of top surface*.—Glabrous.
*Texture of bottom surface*.—Glabrous.
*Appearance of top surface*.—Glossy.
*Appearance bottom surface*.—Glossy.
*Leaf internode length*.—The internodes are extremely close together, forming a basal rosette.
*Color*.—Young foliage upper side: RHS Green 137A. Young foliage under side: RHS Green 138B. Mature foliage upper side: RHS Green 137A. Mature foliage under side: RHS Green RHS 138B.
*Venation*.—Type: Dichotomous; plunging into the limb at the upper surface; raised on the limb at the lower surface. Venation color upper side: RHS Green 138B. Venation color under side: RHS Green 137B.
*Petiole*.—Cross section: Round. Length: Average range 20 to 25 cm. Diameter: Average range 0.3 to 0.8 cm. Pubescence: Slightly tomentose. Color: RHS Green 137A.

Leaf inserted at the nodes of the floral stems:

*Arrangement*.—Biternate.
*Average length*.—15 to 25 cm.
*Average width*.—8 to 15 cm.
*Overall shape of blade*.—Palmatipartite.
*Dissected leaves, describe lobes, quantity of dissection*.—Generally divided in 3 parts, each one of which is further divided in many lobes.
*Apex*.—Acute.
*Base*.—Attenuate.
*Attachment*.—Petiolate.
*Margin*.—Dentate.
*Texture of top surface*.—A little tomentose.
*Texture of bottom surface*.—A little tomentose.
*Appearance of top surface*.—Glossy.
*Appearance bottom surface*.—Glossy.
*Leaf internode length*.—Average 3 to 5 cm.
*Color*.—Foliage upper side: RHS Green RHS 137A. Foliage under side: RHS Green RHS 138B.

*Venation*.—Type: Dichotomous, plunging into the limb at the upper surface and raised on the limb at the lower surface. Venation color upper side: RHS Green 138B. Venation color under side: RHS Green 137B.

*Petiole*.—General: Long, round in cross-section. Length: Average 10 to 20 cm. Diameter: Average 0.3 to 0.5 cm. Pubescence: Slightly tomentose. Color: RHS Yellow-Green 144A.

FLOWER

Quantity per plant: 6 to 8.
Bloom period: Winter to Spring.
Vase life (cut flower): 20 to 25 days.
Persistent or self-cleaning: Self-Cleaning.
Bud:

*Closed bud*.—Shape: Flattened globular with a sharp point. Length: Average 0.5 to 1.5 cm. Diameter: Average 0.3 to 0.5 cm. Color: RHS Yellow-Green 145C.

*Slightly open bud*.—Shape: Flattened globular. Length: Average 1.5 to 3.0 cm. Diameter: Average 2.0 to 3.0 cm. Color: RHS Purple N79D.

Flower:

*Fully open diameter*.—Average 6 to 8 cm.
*Fully open height*.—Average 3 to 4 cm.

Corolla: Round, regular, in cross-section.
Petals:

*Arrangement*.—Imbricated, disposed on the receptacle in very tight verticils. The size of the petals is quite variable, according to the position in the corolla, decreasing from the exterior toward the center.
*Average size*.—
*Lobe length*.—Average 3.5 to 4.5 cm.
*Lobe width*.—Average 3.5 to 4.0 cm.
*Quantity*.—Double flower, petals are very numerous (>100).
*Texture*.—Silky, thin, resistant.
*Lobe apex*.—Rounded.
*Lobe shape*.—Obovate.
*Margin*.—Finely Crenate or entire.
*Aspect*.—Concave.
*Color when opening*.—Upper surface: Near RHS White N155B. Lower surface: Near RHS White N 155B flushed Purple N79D.
*Color fully opened*.—Upper surface: Near RHS White N155B, lightly striated Purple N79D. Lower surface: Near RHS Purple N79D and N79C, striated together. Basal striation near White 155A.

Calyx/sepals:

*Quantity per flower*.—5 or 7.
*Shape*.—Rounded deltate.
*Length*.—Average 2.0 to 3.0 cm.
*Width*.—Average 1.0 to 1.2 cm.
*Apex*.—Acute.
*Base*.—Truncate.
*Margin*.—Entire.
*Texture*.—Lower surface: Tomentose. Upper surface: Glabrous.
*Color*.—Upper Surface: RHS Yellow-Green 146B. Lower Surface: RHS Green 138B Peduncle: None.
Pedicel:

*Length*.—Average range 36 to 47 cm.
*Diameter*.—Average range 1.0 to 1.2 cm.
*Color*.—RHS Yellow-Green 144A.
*Orientation*.—Upright.
*Pubescence*.—Slightly tomentose.

Fragrance: None.

REPRODUCTIVE ORGANS

Androecium: Absent.
Gynoecium: The pistils are numerous, short, locked together at the center of the corolla, dome-shaped apocarpous gynoecium.

*Pistil color*.—RHS Purple 79A.
*Nectar glands*.—Absent.

OTHER CHARACTERISTICS

Disease resistance: Not observed.
Drought tolerance and cold tolerance: No differences have been noted in comparison to the common tolerance characteristics to other *Ranunculus* cultivars.
Fruit/seed production: Not observed.

What is claimed is:

1. A new and distinct cultivar of *Ranunculus* plant named 'ABORIONE' as herein illustrated and described.

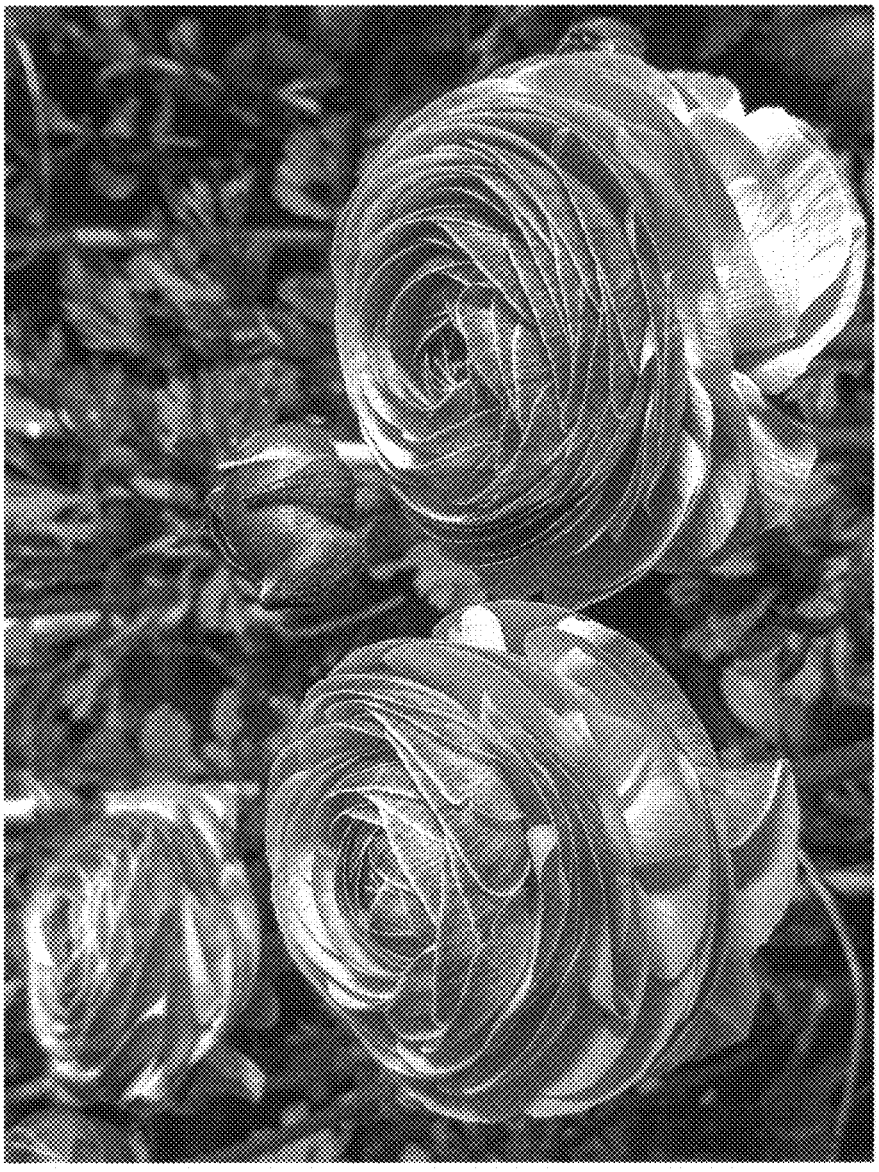

* * * * *